US007067165B2

(12) United States Patent
Hartle et al.

(10) Patent No.: US 7,067,165 B2
(45) Date of Patent: *Jun. 27, 2006

(54) DIMETALHYDROXY MALATE FORTIFIED FOOD MATRICES

(75) Inventors: Jennifer Hartle, Harrisville, UT (US); Stephen D. Ashmead, Clinton, UT (US); Robert Kreitlow, Roy, UT (US); Earl Christiansen, South Ogden, UT (US)

(73) Assignee: Albion International, Inc., Clearfield, UT (US)

( * ) Notice: Subject to any disclaimer, the term of this patent is extended or adjusted under 35 U.S.C. 154(b) by 158 days.

This patent is subject to a terminal disclaimer.

(21) Appl. No.: 10/763,053

(22) Filed: Jan. 21, 2004

(65) Prior Publication Data
US 2004/0185087 A1    Sep. 23, 2004

Related U.S. Application Data

(63) Continuation-in-part of application No. 10/310,108, filed on Dec. 4, 2002, now Pat. No. 6,706,904.

(51) Int. Cl.
*A23K 1/175* (2006.01)
*C07C 59/245* (2006.01)
*C07F 7/24* (2006.01)

(52) U.S. Cl. .............................. 426/74; 556/5; 556/28; 556/114; 556/138; 556/147; 562/582

(58) Field of Classification Search ................ 426/74; 556/5, 28, 114, 138, 147; 562/582
See application file for complete search history.

(56) References Cited

U.S. PATENT DOCUMENTS

| 4,461,778 A | 7/1984 | Vialatte nee Geolier .... 426/422 |
| 4,830,862 A | 5/1989 | Braun et al. ................... 426/74 |
| 5,068,421 A | 11/1991 | Horng ......................... 562/583 |
| 5,186,965 A | 2/1993 | Fox et al. ....................... 426/74 |
| 5,298,634 A | 3/1994 | Connor et al. .............. 549/485 |
| 5,389,387 A | 2/1995 | Zuniga et al. ................ 426/74 |
| 5,401,524 A | 3/1995 | Burkes et al. .............. 426/590 |
| 5,422,128 A | 6/1995 | Burkes et al. ................ 426/74 |
| 6,294,207 B1 | 9/2001 | Christiansen et al. ......... 426/74 |
| 6,706,904 B1 * | 3/2004 | Hartle et al. .................... 556/5 |

OTHER PUBLICATIONS

ABSTRACT: Henry MH and GM Pesti, *An Investigation of Calcium Citrate-malate as a Calcium Source for Young Broiler Chicks*, POULT SCI Aug. 2002;81(8):1149-55.
ABSTRACT: Mithieux G, FV Vega, and JP Riou, *The Liver Glucose-6-phosphatase of Intact Microsomes is Inhibited and Displays Signoid Kinetics in the Presence of Alpha-ketoglutarate-magnesium and Oxaloacetate-magnesium Chelates*, J Biol Chem Nov. 25, 1990;265(33): 20364-8.

* cited by examiner

*Primary Examiner*—Porfirio Nazario-Gonzalez
(74) *Attorney, Agent, or Firm*—Thorpe North & Western

(57) ABSTRACT

A mineral fortified food matrix can comprise a dimetalhydroxy malate composition and a food matrix fortified with the dimetalhydroxy malate composition. Additionally, a method of administering a mineral in a bioavailable form to a warm-blooded animal can comprise steps of fortifying a food matrix with a dimetalhydroxy malate composition and orally administering the food matrix to a warm-blooded animal. In one embodiment, the mineral can be calcium and the method of administering calcium in a bioavailable form can comprise fortifying a food matrix with a dicalciumhydroxy malate composition.

22 Claims, No Drawings

DIMETALHYDROXY MALATE FORTIFIED FOOD MATRICES

The present application is a continuation-in-part of U.S. patent application Ser. No. 10/310,108, filed on Dec. 4, 2002 now U.S. Pat. No. 6,706,904, which is incorporated herein by reference in its entirety.

FIELD OF THE INVENTION

The present invention is drawn to dimetalhydroxy malates. More particularly, the present invention is drawn toward dimetalhydroxy malate fortified foods and beverages.

BACKGROUND OF THE INVENTION

Magnesium is a mineral that is needed in humans and other warm-blooded animals for bone, protein, and fatty acid formation. Magnesium is also involved in the formation of new cells, activating certain vitamins, relaxing muscles, clotting blood, and forming ATP. People with diabetes often have magnesium levels that are lower than normal compared with those who have normal glucose tolerance. Supplementation of magnesium can help maintain health in some of these areas, as well as help in overcoming some of these problems. Typically, many people do not consume enough magnesium in their diets.

Calcium, on the other hand, is the most abundant mineral in the human body. Of the calcium contained in the average body, about 99% is located in the bones, including the teeth. Calcium is needed to form bones and teeth and is also required for blood clotting, transmission of signals in nerve cells, and muscle contraction. Calcium supplementation is believed to reduce the incidence of osteoporosis.

Choosing a form of magnesium and/or calcium for supplementation has been a source of some confusion in the industry. Calcium carbonate is one form of calcium that is widely used, but is not believed to be absorbed as well as some other forms. Calcium citrate provides a form that is believed to be better absorbed than calcium carbonate. Calcium citrate/malate (CCM) is believed to be absorbed more fully than carbonate as well.

Other divalent minerals, such as zinc, copper, iron, and manganese, are also known to be important to the human diet, and can be administered in a supplemental form. For example, the trace mineral zinc is known to be involved in the transport of vitamin A, taste, wound healing, and fetal development. Zinc also plays a part in the correct functioning of many enzymes, hormones including insulin, genetic material, and proteins. Copper, on the other hand, plays a role in the absorption of iron, and is part of many enzymes. Additionally, iron is necessary for production or hemoglobin and oxygenation of red blood cells, builds up blood quality, and increases resistance as well as increasing energy production. Benefits of manganese include improvement of memory and reflexes, reducing of fatigue, and promoting proper development of thyroid hormones, skeletal, reproductive, and central nervous systems.

Malic acid is a dicarboxylic acid that is naturally occurring. Malic acid plays a role in the complex process of deriving ATP (the energy currency that runs the body) from food. Malic acid is found in a wide variety of fruits (including richly in apples) and vegetables. As malic acid is already found abundantly in humans and other warm-blooded animals, it can be administered without adverse affects. Further, there is some evidence that malic acid supplementation can be helpful to human nutrition.

SUMMARY OF THE INVENTION

It has been recognized that the use of certain complexes can provide a bioavailable form of minerals for food and beverage fortification. Specifically, a mineral fortified food or beverage can comprise a dimetalhydroxy malate composition, and a food matrix fortified with the dimetalhydroxy malate composition.

Additionally, a method of administering a mineral in a bioavailable form to a warm-blooded animal can comprise steps of fortifying a food matrix with a dimetalhydroxy malate composition, and orally administering the food matrix to a warm-blooded animal.

In either of the above embodiments, the dimetalhydroxy malate composition can be dicalciumhydroxy malate.

Additional features and advantages of the invention will be apparent from the following detailed description which illustrates, by way of example, features of the invention.

DETAILED DESCRIPTION OF THE PREFERRED EMBODIMENT(S)

Before the present invention is disclosed and described, it is to be understood that this invention is not limited to the particular process steps and materials disclosed herein because such process steps and materials may vary somewhat. It is also to be understood that the terminology used herein is used for the purpose of describing particular embodiments only. The terms are not intended to be limiting because the scope of the present invention is intended to be limited only by the appended claims and equivalents thereof.

It is to be noted that, as used in this specification and the appended claims, the singular forms "a," "an," and "the" include plural referents unless the context clearly dictates otherwise.

The term "nutritionally relevant metal" or "nutritionally relevant divalent metal" means any divalent metal that can be used as part of a nutritional supplement, is known to be beneficial to humans and other warm-blooded animals, and is substantially non-toxic when administered in traditional amounts, as is known in the art. Examples of such metals include copper, zinc, manganese, iron, magnesium, calcium, and the like.

When referring to a dimetalhydroxy malate, the "di" portion of the name refers to two $^+$M(OH) or metalhydroxy groups, one being complexed to a first carboxyl group of the malate ion, and the other being complexed to a second carboxyl group of the malate ion. Thus, each metal is complexed to the malate ion and is also complexed to its own hydroxy group to charge balance the metal. The metals that can be used include divalent nutritionally relevant metals, and two of the same metal or two different metals can be present at the two different carboxyl groups of the malate ion, respectively. Examples of such metals include copper, zinc, manganese, iron, magnesium, calcium, and the like.

When referring to a dicalciumhydroxy malate, the "di" portion of the name refers to two $^+$Ca(OH) or calciumhydroxy groups, one being complexed to a first carboxyl group of the malate ion, and the other being complexed to a second carboxyl group of the malate ion.

The term "divalent calcium-containing composition" shall mean compositions used to react with malic acid to form a dicalciumhydroxy malate in accordance with embodiments of the present invention. Examples of such compositions include calcium hydroxide, calcium oxide, and calcium carbonates.

The terms "food matrix" or "food matrices" include foods, beverages, dehydrated food mixes, beverage mixes, and the like.

In accordance with these definitions, a mineral fortified food or beverage can comprise a dimetalhydroxy malate composition, and a food matrix fortified with the dimetalhydroxy malate composition. In one embodiment, the dimetalhydroxy malate composition can have the structure of Formula 1 below:

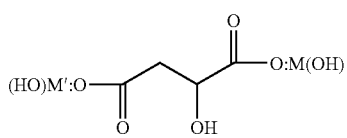

Formula 1 wherein M' and M are independently nutritionally relevant divalent metals, such as copper, zinc, manganese, iron, magnesium, calcium, or the like.

The present invention is also drawn toward a method of administering a mineral in a bioavailable form to a warm-blooded animal. In one embodiment, the composition of Formula 1 above can be administered to the warm-blooded animal, such as a human. As the present invention is drawn primarily toward the fortification of a food matrix, the administration route is typically by oral administration. Many different food matrices can be used, including foods, drinks, dehydrated food mixes, dry drink mixes, or other substances acceptable for oral consumption. Examples of food matrices that can be fortified include natural cereal grain such as barley, corn, millet, oats, quinoa, rice, rye, sorghum, triticale, wheat and wild rice; processed cereal grain such as cereal flakes, puffed cereal grain kernels, puffed dough cereal, extruded dough cereal, baked cereal, nuggets and rolled grain cereal, and cereal breads; oleaginous foods such as margarine, butter, lard, vegetable oil spread, and oil; dairy products such as whole milk, low-fat milk, non-fat milk, flavored milk, cheese, processed cheese, yogurt, frozen yogurt, cream, sour cream, and ice cream; food bars such as energy bars, weight loss bars, snack bars, and granola bars; beverages such as energy drinks, sports drinks, citrus drinks, fruit drinks, and carbonated drinks; beverage mixes such as fruit mix and citrus mix; and legumes such as peas and beans. Fortification can be by coating, admixing, absorbing, adsorbing, or by another known fortification method.

Additionally, calcium can be a metal utilized in the dimetalhydroxy malate, where a calcium fortified food or beverage is desired. Such a composition can comprise a dicalciumhydroxy malate composition, and a food matrix fortified with the dicalciumhydroxy malate composition. In one embodiment, the dicalciumhydroxy malate composition can have the structure of Formula 2 below:

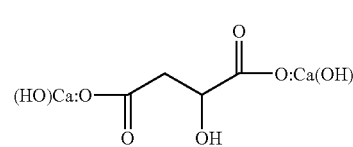

Formula 2

The present invention is also drawn toward a method of administering calcium in a bioavailable form to a warm-blooded animal. In one embodiment, the composition of Formula 2 above can be administered to the warm-blooded animal, such as a human. Again, as the present invention is drawn primarily toward the fortification of a food matrix, the administration route is typically by oral administration. The many different food matrices listed above can also be fortified with the dicalciumhydroxy malate composition having the structure of Formula 2.

No matter what the vehicle of delivery, the fortified foods, beverages, or beverage mixes of the present invention can be made to be stable and palatable, even when coadministered with other fortificants such as mineral salts and/or mineral amino acid chelates. In one embodiment, the food matrix can also be fortified with an iron source, such as an iron amino acid chelate.

There are several specific reaction schemes that can be followed in making the composition of Formula 1, though these reaction schemes are not intended to be limiting. In one embodiment, these three reaction schemes can utilize calcium as the model metal, as is shown in Formula 2. In accordance with this, a first reaction scheme is depicted below in Formula 3, as follows:

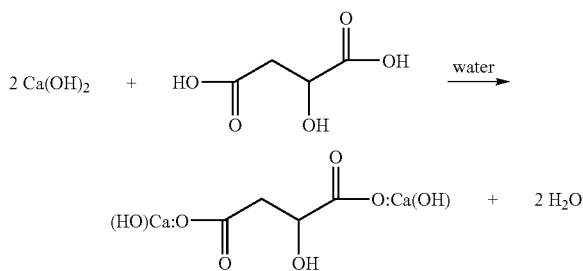

Formula 3

In the above reaction scheme, two extra water molecules are formed as the hydrogen atoms are liberated from the malic acid and react with the excess hydroxy groups from the two calcium hydroxides. A second reaction scheme is depicted below in Formula 4, as follows:

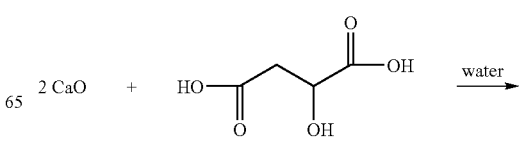

Formula 4

-continued

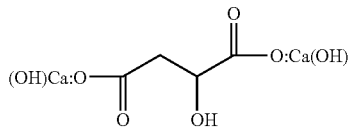

In Formula 4 above, when a metal oxide is used, no extra water molecules are formed. In a third reaction scheme, dicalciumhydroxy malate can be prepared in accordance with Formula 5, as follows:

Formula 5

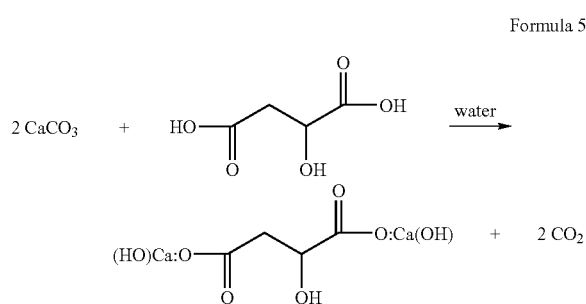

In the above reaction scheme, as shown, when a metal carbonate is used, two carbon dioxide molecules are formed.

Though preparative schemes for dicalciumhydroxy malate is shown in Formulas 3 to 5, other metals can be used, such as other nutritionally relevant divalent metals. Additionally, other preparative schemes can be used as would be known in the art. For example, divalent metals that can exist in an elemental form, e.g., copper, can be prepared from its native or elemental state.

With respect to each of the compositions and methods of the present invention, once formed in an aqueous solution, the product can be dried to form a particulate composition. Desired particulate sizes can be formed using one of a number of drying methods, including spray drying, drum drying, tray drying, tunnel drying, freeze drying, compressed air drying, and oven drying, among others as is known in the art. Such dry particulates can be used to fortify particularly dry beverage mixes, dehydrated food mixes, and the like. These drying processes can result in particle sizes ranging from 20–200 mesh, however, some of these methods may require an additional grinding or classification step. Spray drying is an example of a drying method that does not require a grinding step, and can result in particulates having a smaller size distribution, e.g., from 80–100 mesh. If it is not desired to have a particulate fortificant, then the particles can be suspended or solubilized in a solution for other forms of fortification.

Alternatively, the dimetalhydroxy malate compositions of the present invention can also remain in solution, e.g., without a drying step, for coating or absorbing the fortificant onto or into a food matrix. An example would be the fortification of rice, where a liquid composition containing dicalciumhydroxy malate could be coated on the surface of individual rice grains.

In the above Formulas 3–5, the reactions shown are in the presence of excess water or $CO_2$. These byproducts can be removed, such as by bubbling off in the case of the carbon dioxide gas or drying in the case of water. In other embodiments, if excess hydrogen or other ions are present, they can be neutralized or otherwise removed. Alternatively, some of these byproducts can remain in solution as may be desired for a specific food matrix fortification application. Though these reactions are shown in the presence of excess water, the same reaction schemes can be prepared in the absence of excess water. In other words, small amounts of water can be added incrementally to the reactants to form a granular product, thereby removing the need for a spray-drying step (or other equivalent drying step), if a dried product is desired. For example, the reacting step can be carried out by (a) dry blending particulate malic acid and a particulate divalent metal-containing composition to form a particulate blend; (b) adding water to the particulate blend in an amount that causes a partial reaction between the malic acid and the divalent metal-containing composition, (c) allowing the particulate blend to substantially react in the presence of the amount of water; and (d) repeating step (b) and step (c) until a granular product is formed that is substantially fully reacted.

In one embodiment, this process can be carried out by first, combining the reactants, i.e., malic acid and divalent metal-containing composition, in dry form and mixing them together, such as in a ribbon blender or the like. The mixing device can be continuously run during this process for acceptable results. A fraction of the total amount of water needed to effectuate the reaction can then be slowly added, such as by spraying the water into the particulate mixture. The water can be evenly sprayed or poured over the mixture for providing a substantially uniform liquid content throughout the mixture, whereas dumping or unevenly pouring water onto the reactants can cause over reaction in certain areas of the mixture as well as unfavorable clumping. In one embodiment, from 5% to 20% of the water necessary to complete the reaction can be added or sprayed on at a time, allowing reaction time to occur between each further water addition. A water jacket can be used with the reaction vessel to keep the reactants cool.

As the water is added in small amounts stepwise, the product will progress toward completion. At each stage of added water, the reactants tend to become sponge-like and raise in level within the mixer. When the reaction nears completion for a given stage, the heat lowers, the product level falls, and the density increases, returning the product to a more granular state. Next, more water is added, and a similar phenomenon reoccurs (typically to a lesser extent at each water addition step). At each stage, the product should be allowed to react until the reaction is substantially complete. Once the heat and expansion is substantially absent when water is added, the process is done. At this point, if water is continued to be added, the product will begin to change back to a powder form, which is undesirable. Therefore, care should be taken to stop adding water when desired granulation is present, and the reaction has substantially stopped. Upon completion of the process, the product can be removed from the mixing device, stored in either a cool or warm room for drying, and optionally, ground to a desired particle size. These processes for granulation can result in particle sizes ranging from 8–80 mesh. Additionally, the process of granulation can be configured to result in particle sizes ranging from 20–40 mesh.

Coloring agents, such as titanium dioxide, may optionally be included when appropriate. For example, when coating white rice with a dimetalhydroxy malate, discoloration may occur such that the use of titanium dioxide acts as a whitening agent to reduce the discoloration. Alternatively, various food coloring agents can be used in the various food matrices for achieving colors that are visually stimulating or desirable.

The food matrices may further comprise a food grade antioxidant in an amount sufficient to inhibit oxidation of materials, especially lipids, on the surface of the cereal grain. Excessive oxidation can contribute to off-flavor development and off-odors. Known or conventional antioxidants include, but are not limited to, butylated hydroxyanisole (BHA), butylated hydroxytoluene (BHT), tert-butylhydroquinone (TBHQ), rosemary extract, and mixtures thereof.

To further enhance oxidative stability, the fortified food matrices should be packaged in a moisture impenetrable container. Such containers include foil linked packages, metal cans, and plastic or laminate packages. The fortified food matrices can be packaged under nitrogen, carbon dioxide, or other inert non-oxidizing gases to further enhance oxidative stability and shelf life. Such packaging methods are well known in the art.

Additionally, a flavoring or aroma agent may also be added to the food matrices in amounts that are organoleptically pleasing. For example, a calcium fortified food matrix can be flavored or enhanced with any naturally or synthetically prepared fruit or botanical flavors, aroma compounds, or mixtures thereof.

EXAMPLES

The following examples illustrate some of the embodiments of the invention that are presently known. While the invention is drawn to dimetalhydroxy malate mineral fortifications, the examples utilize calcium as a model metal. Thus, these examples should not be considered as limitations of the present invention, but are merely in place to teach how to make the best-known compositions of the present invention based upon current experimental data. As such, a representative number of compositions and their method of manufacture are disclosed herein.

Preparation of Dimetalhydroxy Malate Compositions for Food Matrix Fortification

Example 1

An aqueous solution of malic acid is prepared by mixing 14.79 g of malic acid with 25 mL of water until the solution is clear. Also, in a separate container an aqueous solution of calcium hydroxide is prepared by thoroughly mixing 16.34 g of calcium hydroxide in 25 mL of water. The calcium hydroxide solution is then added into the malic acid solution. The resulting liquid product is a dicalciumhydroxy malate-containing aqueous solution having a slight yellow color.

Example 2

An aqueous solution of malic acid is prepared by mixing 134.09 g of malic acid with 25 mL of water until the solution is clear. Next, 112.18 g of particulate calcium oxide is slowly added into the aqueous malic acid mixture while stirring continuously. The resultant aqueous mixture is stirred for 45 minutes prior to being spray dried. The resulting product is a dicalciumhydroxy malate powder.

Example 3

A large batch of dicalciumhydroxy malate is produced by mixing 19.16 kg of malic acid in 68.19 L of water. In a separate tank, 16.33 kg of calcium oxide is mixed in 68.19 L of water. These two aqueous solutions are slowly mixed together and stirred continuously. A milky solution containing the product resulted, which is spray dried to obtain a powdered product of dicalciumhydroxy malate.

Example 4

An aqueous solution of malic acid is prepared by mixing 134.09 g of malic acid with 50 mL of water. An aqueous solution of calcium carbonate is also prepared in a separate container by thoroughly mixing 200.18 g of calcium carbonate in 50 mL of water. The aqueous calcium carbonate solution is then slowly added to the aqueous malic acid solution. The resulting liquid is spray dried to produce a powdered dicalciumhydroxy malate.

Example 5

A dicalciumhydroxy malate granular product is prepared by mixing two molar equivalents of particulate calcium hydroxide with one molar equivalent of particulate malic acid (totaling 45 kg for the entire composition) in a ribbon blender for 15 minutes at normal speeds. To ensure that the product does not over react when small amounts of water are added to the batch a water jacket is used. Next, about 1 L of water is slowly sprayed into the particulate mixture product. After about 10 minutes of reaction time (the product becomes spongy and rises, and then drops back to a more granular state), an additional 1 L of water is added. This is repeated several times until no further reaction appeared to be occurring upon addition of water. The end result is a granular product. Once a fully reacted granular product is formed, no additional water is added. The resulting composition is then dried in a cool room and ground to a predetermined particle size.

Example 6

An aqueous solution of malic acid is prepared by mixing 5.859 kg of malic acid with 18.18 L of water until the solution is clear. An aqueous solution of magnesium oxide is also prepared in a separate container by thoroughly mixing 3.515 kg of magnesium oxide in 18.18 L of water. The magnesium oxide solution is then slowly added to the malic acid solution. The resulting solution is cooled, and then spray dried to produce a powdered dimagnesiumhydroxy malate.

Example 7

An aqueous solution of malic acid is prepared by mixing 134.09 g of malic acid with 50 mL of water. An aqueous solution of copper(II)hydroxide is also prepared in a separate container by thoroughly mixing 195.12 g of copper(II) hydroxide in 50 mL of water. The copper(II)hydroxide solution is then slowly added to the malic acid solution. The resulting solution is spray dried to produce a powdered dicopper(II)hydroxy malate.

Example 8

An aqueous solution of malic acid is prepared by mixing 134.09 g of malic acid with 50 mL of water. An aqueous solution of zinc oxide is also prepared in a separate container by thoroughly mixing 162.78 g of zinc oxide in 50 mL of water. The zinc oxide solution is then slowly added to the malic acid solution. The resulting solution is spray dried to produce a powdered dizinchydroxy malate.

Example 9

An aqueous solution of malic acid is prepared by mixing 134.09 g of malic acid with 50 mL of water. Next, 111.69 g of ferronyl powder is added to the malic acid solution. The solution is stirred for approximately 2 hours. The resulting solution is then spray dried to produce a powdered dihydroxyferrous malate.

Food Matrix Fortification Using Dimetalhydroxy Malates

Examples 10 to 26 deal with fortifying various food matrix products with dicalciumhydroxy malate compositions. However, it is understood, and often preferred, that other minerals can also be fortified therewith. For example, the fortification of a food, beverage, dehydrated food mix, or beverage mix with a dicalciumhydroxy malate can be accompanied by fortification using other metal sources, such as metal amino acid chelates, metal salts, or the like. In some embodiments it may be desired to include iron bisglycinate amino acid chelates, or other chelates or salts therewith to provide multiple bioavailable sources of mineral nutrition.

Example 10

The following is a method for fortifying white rice with dicalciumhydroxy malate using a spraying method. First, 380 grams of hydroxypropyl cellulose is dry blended with 7.5 kilograms of dicalciumhydroxy malate prepared in accordance with Example 2. To the dry ingredients, 20 kilograms of water and 4 kilograms of isopropyl alcohol are added and mixed under sheer and good agitation until the solution becomes clear and homogenous. Next, 250 pounds of rice are placed in a revolving coating pan. While forced hot air is blown into the pan, the solution containing the dicalciumhydroxy malate is sprayed onto the rice until all of the solution is evenly applied. The rice is dried to less than 11% moisture and removed from the coating pan to complete the batch. From this process, 250 pounds of rice is fortified with dicalciumhydroxy malate having a calcium content of about 30% by weight. The recommended rate is 1,000 milligrams of calcium per pound of rice. Therefore, the 250 pounds of coated rice are then admixed with 1200 pounds of untreated rice. By evenly mixing coated rice with uncoated rice at this rate, a rice mixture is produced having a calcium content of about 1,000 milligrams of calcium per pound of mixed rice.

Example 12

The following is a method for producing calcium fortified oven baked cereal rice. Initially, a rice mixture is prepared by mixing 100 pounds of medium rice with 15 pounds of table sugar (sucrose), 1 pound of table salt (NaCl), 4 pounds of malt syrup, and sufficient water to obtain a 20% moisture content. The mixture is cooked in a pressurized batch cooker for 1 hour at 15–18 psi. The rice mixture is then conveyed to smoothing wheels where it is allowed to cool. The rice mixture is then run over a drum dryer until the moisture is decreased from 20% to 10% and then is tempered at room temperature for 6 hours. The rice is bumped on flaking rolls and dried a second time down to 6% moisture. Next, the rice is baked at 600° F. for 90 seconds, conveyed through flaking wheels and spread into a thin layer. While being conveyed, a continuous coating spray is applied to the processed rice, where the coating includes 10 pounds of water, 3 pounds of table sugar, a 2 ounce vitamin blend, and 1330 grams of dicalciumhydroxy malate prepared in accordance with Example 2. The product is allowed to dry and is then packaged. The result is a product having approximately 250 mg of calcium per 1 ounce serving.

Example 13

Calcium fortified puffed corn is prepared by the following general procedure. The process begins with mixing 100 pounds of corn flour, 2 pounds of table salt, 2 pounds of starch, 5 grams of FD&C yellow color, 20 pounds of water, and 2 pounds of malt syrup. The mixture is conveyed to a cooking extruder where it is extruded to a desired shape. The mixture is dried to lower the moisture from 20% to 10%, tempered, and then loaded into a puffing gun where it is pressurized to 200 psi. The firing process is then carried out where the puffed corn is caught and screened to a desirable size. The puffed corn is dispersed in a thin layer where a continuous spray, including 10 pounds of water, 3 pounds of dextrose, a 2 ounce vitamin blend, and 1330 grams of dicalciumhydroxy malate prepared in accordance with Example 2, is applied to the puffed corn. Once coated, the puffed corn is dried until the product reaches a 2% moisture level to be packaged. The result is a product having approximately 250 mg of calcium per 1 ounce serving.

Example 14

Calcium fortified puffed rice is prepared by the following general process. Initially, 1330 grams of dicalciumhydroxy malate prepared in accordance with Example 2 are admixed with a 2 ounce vitamin blend and 4 pounds of water to form an aqueous solution. About 100 pounds of long grain white rice is soaked in the aqueous solution for about 1 hour. A puffing gun is preheated to 475° F. and then the soaked rice is loaded into the pressurized puffing gun (200 psi). The firing process is started and the puffed rice is caught and screened to obtain a desirable size. The puffed rice is dried in an oven until the product reaches 2% moisture for packaging. The end result provides a puffed rice product having approximately 250 mg of calcium per 1 ounce serving.

Example 15

Calcium fortified extruded wheat shapes are prepared by the following general procedure. Initially, 18 pounds of water are mixed with 2 pounds of malt syrup to form a slurry. Next, 100 pounds of wheat flour, 10 pounds of table sugar, 2 pounds of table salt, 10 grams of FD&C color, a 2 ounce vitamin blend, and 1330 grams of dicalciumhydroxy malate prepared in accordance with Example 2 are mixed into the slurry. The mixture is then conveyed into a cooking extruder and extruded into appropriate shapes (such as shredded wheat or other common grain shapes) at 17–18% moisture. The product is further conveyed into an oven for toasting at 575° F. for 90 seconds. The product is allowed to cool and then packaged. The resulting product provides approximately 250 mg of calcium per 1 ounce serving.

Example 16

Calcium fortified toasted corn flakes are prepared by the following general procedure. First, the process begins with mixing 6 pounds of table sugar, 2 pounds of table salt, a 2 ounce vitamin blend, and 1330 grams of dicalciumhydroxy malate prepared in accordance with Example 2 with 2 pounds of malt syrup and water to obtain a moisture level of about 32%. The resulting syrup is mixed with 100 pounds of corn grits and placed in a batch pressure cooker at 15–18 psi for 2 hours. The corn grits are placed onto a conveyer and run under smoothing wheels. The smoothed product is moved into a drier with controlled airflow and humidity at 220–230° F. until the moisture reaches 10–14%. The product is then air cooled until it reaches ambient temperature where it is tempered for an additional 3 hours. The paste or dough is then rolled into a thin layer and toasted at 575° F. for 90 seconds. Once removed, the toasted dough is cooled and flaked to an appropriate size in preparation for packaging. The end result provides a toasted corn flake product having approximately 250 mg of calcium per 1 ounce serving.

Example 17

Calcium fortified 80% soft margarine is prepared by mixing a fat phase and a water phase at 8:1 ratio by weight through the following general process. A mixture of the fat phase consisting of partially hydrogenated soybean oil (22% by total weight), liquid soybean oil (58% by total weight), lecithin (Actiflo 68UB) (0.2% by total weight), emulsifier (Dimodan PVP) (0.2% by total weight), and beta carotene (color and vitamin A) (0.003% by total weight) is heated to 50° C. A mixture of the water phase consisting of water (12% by total weight), salt (1% by total weight), non-fat dry milk (1% by total weight), dicalciumhydroxy malate prepared in accordance with Example 2 (2% by total weight), potassium sorbate (0.1% by total weight), citric acid (0.05% by total weight), and natural or artificial butter flavor (0.1% by total weight) is heated to 50° C. To prepare the emulsion, the water phase is added to the fat phase with high sheer and the emulsion is run through a scrape surface heat exchanger. The product of the emulsion is then packaged and tempered at 5° C. for 24–48 hours. This 80% soft margarine is fortified with approximately 250 mg calcium per ounce. The calcium fortified margarine prepared as described above is palatable and is stable at refrigerated temperature for up to four months.

Example 18

This formulation for American pasteurized process cheese fortified with a dicalciumhydroxy malate prepared in accordance with Example 2 will provide a product having about 400 mg of calcium per 1 ounce serving.

| Weight % | Ingredients |
|---|---|
| 87.% | blended American cheeses |
| 1% | salt |
| 8% | water |
| 1% | sodium citrate |
| 0.15% | sodium phosphate |
| 0.15% | sodium pyrophosphate |
| 0.2% | annatto color |
| 2.0% | dicalciumhydroxy malate prepared in Example 2 |

A dicalciumhydroxy malate fortified American pasteurized process cheese is prepared by selecting a blend of mild, medium, sharp chedders and jack cheeses that delivered a desired flavor profile (this may be modified according to taste preference). The cheeses are warmed to room temperature and then ground into fine pieces. The ground-up cheese pieces are placed into a steam cooker under slow agitation until the cheese is melted throughout. Water is added to the cheese to attain a 40% moisture level. The salt, color, and the dicalciumhydroxy malate prepared in accordance with Example 2 are then added. Emulsifying salts are then added to the mixture before the temperature reached 120° F. The pH level should remain between 5.6 and 6.0. However, if the pH level rises above 6.0, small amounts of lactic acid may be added to reduce the pH level. The entire batch is cooked until the temperature reached 170° F. for about 3 minutes. The batch is then poured into a filler where the pH and moisture levels are once again confirmed. The product may be filled into desired size packages or formed into slices. Finally, the packaged cheese is tempered at room temperature for 4 to 18 hours.

Example 19

This formulation for low-fat frozen yogurt fortified with dicalciumhydroxy malate prepared in accordance with Example 2 will provide a product having about 400 mg of calcium per 4 fl oz. of low-fat frozen yogurt.

| | Mix Portion |
|---|---|
| Weight % | Ingredients |
| 79.5% | milk standardized to 2% milk fat and 11% milk solids non-fat |
| 12% | sugar |
| 1% | whey protein concentrate |
| 6% | corn syrup solids |
| 0.4% | stabilizer/emulsifier |
| 0.6% | flavoring |
| 0.5% | dicalciumhydroxy malate prepared in Example 2 |

| | Yogurt Portion |
|---|---|
| Weight % | Ingredients |
| 99.7% | milk standardized to 11% milk solids non-fat |
| 0.3% | culture |

A dicalciumhydroxy malate fortified low-fat frozen yogurt is prepared by blending the mix portion with the yogurt portion at a 4:1 ratio by weight. The mix portion is prepared by standardizing the milk, milk fat, and milk solids to the prescribed levels. Under good agitation, dry ingredients including the dicalciumhydroxy malate prepared in accordance with Example 2 are admixed into the milk (excluding the flavoring). This mixture is pasteurized at 190° F. for 45 seconds and homogenized at 1,500 psi. The product is then cooled to about 38–40° F. and held in a blending tank.

The yogurt portion is prepared by standardizing the milk and milk solids to the prescribed levels where they are pasteurized at 195° F. for 3–6 minutes and homogenized at 1000 psi. The product is then cooled to about 107–112° F. where it is inoculated with the starter culture. The tank is held at about 105–108° F. until the pH reached 4.6. At this point, the acidic product is gently agitated and cooled to about 40–45° F.

Once both the mix portion and the yogurt portion are complete, they are blended through a smoothing valve (20% yogurt portion by weight and 80% mix portion by weight). The blend is held in a tank under slow agitation for 4 hours.

Once complete, flavors are mixed into the yogurt product, which is then sent to the continuous freezer set at 80% overrun.

Example 20

This formulation for ice cream fortified with dicalciumhydroxy malate prepared in accordance with Example 2 will provide a product having about 250 mg of calcium per 4 fl oz. of ice cream.

| Weight % | Ingredients |
|---|---|
| 55.85% | milk |
| 20% | cream standardized to 40% milk fat |
| 6% | non-fat dry milk |
| 12% | sugar |
| 5% | corn syrup solids |
| 0.4% | stabilizer/emulsifier |
| 0.5% | flavor and coloring |
| 0.5% | dicalciumhydroxy malate prepared in Example 2 |

A dicalciumhydroxy malate fortified ice cream product is prepared by standardizing the milk, milk fat, and milk solids to the prescribed levels. Under good agitation, the dry ingredients including the dicalciumhydroxy malate prepared in accordance with Example 2 are added. The product is pasteurized at 180° F. for 35 seconds and homogenized at 2200 psi. Next, the pasteurized and homogenized product is cooled to about 38–40° F. and held in a storage tank for from 4 to 24 hours. The flavor and color are then mixed into the vat containing the product. Once complete, the ice cream product is then sent to the continuous freezer set at 100% overrun.

Example 21

This formulation for energy bars fortified with dicalciumhydroxy malate prepared in accordance with Example 2 will provide a product having about 150 mg of calcium per 50 g serving of energy bar. The following formulations are for three different energy bars prepared for different tastes.

| Milk Chocolate Peanut Butter Bar | |
|---|---|
| Weight % | Ingredients |
| 13% | soy protein isolate |
| 10% | whey powder |
| 5% | 10 D.E. maltodextrin |
| 12% | crystalline fructose |
| 10% | sucrose |
| 2% | nonfat dry milk |
| 13% | corn syrup 42 D.E. |
| 2% | peanut flour |
| 6% | peanut butter |
| 4% | partially hydrogenated soybean oil |
| 2% | honey |
| 5% | densified crisp rice #110 |
| 0.1% | salt |
| 0.5% | lecithin |
| 0.6% | vitamin & mineral blend |
| 0.4% | butter vanilla flavor |
| 0.4% | natural flavor blend |
| 10% | water |
| 4% | dicalciumhydroxy malate prepared in Example 2 |

| Black & White Chocolate Bar | |
|---|---|
| Weight % | Ingredients |
| 13% | soy protein isolate |
| 10% | whey powder |
| 8% | 10 D.E. maltodextrin |
| 13% | crystalline fructose |
| 10% | sucrose |
| 3% | nonfat dry milk |
| 13% | corn syrup 42 D.E. |
| 5% | dark cocoa |
| 4% | partially hydrogenated soybean oil |
| 2% | honey |
| 5% | densified crisp rice |
| 0.1% | salt |
| 0.5% | lecithin |
| 0.6% | vitamin & mineral blend |
| 0.4% | butter vanilla flavor |
| 0.4% | natural flavor blend |
| 8% | water |
| 4% | dicalciumhydroxy malate prepared in Example 2 |

| DBL Dark Chocolate Crunch Bar | |
|---|---|
| Weight % | Ingredients |
| 13% | soy protein isolate |
| 10% | whey powder |
| 6% | 10 D.E. maltodextrin |
| 15% | crystalline fructose |
| 10% | sucrose |
| 3% | nonfat dry milk |
| 13% | corn syrup 42 D.E. |
| 5% | dark cocoa |
| 4% | partially hydrogenated soybean oil |
| 2% | honey |
| 5% | densified crisp rice |
| 0.1% | salt |
| 0.5% | lecithin |
| 0.6% | vitamin & mineral blend |
| 0.4% | butter vanilla flavor |
| 0.4% | natural flavor blend |
| 8% | water |
| 4% | dicalciumhydroxy malate prepared in Example 2 |

For each of the preceding formulations for dicalciumhydroxy malate energy bars, a general preparation procedure is followed. Initially, a slurry of water, corn syrup, sucrose, fructose, soybean oil and honey is formed in a blend tank. To this slurry, either peanut butter (milk chocolate peanut butter bar) or dark cocoa (black and white chocolate bar or DBL dark chocolate bar) is added. The slurry is then heated up to 120° F., and placed in a dough mixer. The other dry ingredients are then added to the slurry, and the batch is mixed until homogenous. Next, the flavors and crisp rice are added and mixed until dispersed.

The resulting blended mass is then loaded into an extruder and extruded to a predetermined size. The extruded bars are then run under refrigerated air blast to cool. Once cooled, the bars are coated with milk chocolate (milk chocolate peanut butter bar), white chocolate (black and white chocolate bar) or dark chocolate containing crisp rice (DBL dark chocolate crunch bar). The weight ratio of chocolate coating to extruded center is 1:2 (or 50 pounds of chocolate coating to 100 pounds of extruded center).

Example 22

The formulation for a liquid energy drink fortified with dicalciumhydroxy malate prepared in accordance with Example 2 will provide a product having about 150 mg of calcium per 8-fl oz. of liquid energy drink.

Vanilla Flavored Drink

| Weight % | Ingredients |
|---|---|
| 4% | 10 D.E. maltodextrin |
| 9% | sucrose |
| 8% | nonfat dry milk |
| 0.25% | sodium citrate |
| 0.02% | carrageenan |
| 0.6% | vitamin & mineral blend |
| 0.55% | vanilla flavor |
| 76.3% | filtered water |
| 1.1% | dicalciumhydroxy malate prepared in Example 2 |

A liquid energy drink fortified with dicalciumhydroxy malate is prepared through the following general procedure. Initially, sucrose, nonfat dry milk, maltodextrin, sodium citrate, carrageenan, vitamins and minerals, and dicalciumhydroxy malate prepared in accordance with Example 2 are blended into water under good agitation. To this aqueous liquid, vanilla flavor is added, and the complete mixture is heat treated to 165° F. and homogenized. The resulting product is cooled to 40° F. and packaged.

In the alternative, a powdered drink fortified with dicalciumhydroxy malate is prepared by having all dry ingredients blended together as a premix for subsequent mixing with an appropriate amount of water or milk. In other alternatives, various other flavorings can be substituted for the vanilla flavor, and can be prepared in substantially similar processes.

Example 23

A formulation for a sports drink fortified with dicalciumhydroxy malate prepared in accordance with Example 2 will provide a product having about 200 mg of calcium per 8-fl oz. or sports drink.

Fruit Punch Flavored Sports Drink

| Weight % | Ingredients |
|---|---|
| 2.7% | 42 D.E. corn syrup |
| 3.5% | sucrose |
| 0.3% | citric acid |
| 0.1% | salt |
| 0.5% | fruit punch flavor |
| 91.25% | filtered water |
| 1.65% | dicalciumhydroxy malate prepared in Example 2 |

A fruit punch flavored sports drink fortified with dicalciumhydroxy malate is prepared by the following general procedure. Initially, sugar, corn syrup citric acid, salt, dicalciumhydroxy malate prepared in accordance with Example 2 are blended into water under good agitation. To this aqueous liquid, a fruit punch flavoring is added. The complete batch is heat treated to 150° F., and allowed to cool to 40° F. prior to being packaged. In other alternatives, various other flavorings can be substituted for the fruit punch flavor, and can be prepared in substantially similar processes.

Example 24

A calcium and vitamin D supplement powdered drink mix that yields 500 mg of calcium and 200 IU vitamin D per 7 g serving can be prepared as follows.

Orange Flavored Aspartame/Ace K Sweetened Drink Mix

| Weight % | Ingredients |
|---|---|
| 25% | maltodextrin |
| 7.68% | sodium bicarbonate |
| 17.4% | citric acid |
| 0.08% | aspartame |
| 0.08% | acesulfame potassium (Ace K) |
| 0.20% | Vitamin D3 (100,000 IU/g) |
| 3.6% | N & A orange flavor** |
| 25.10% | dicalciumhydroxy malate prepared in Example 2 |

An orange flavored aspartame/Ace K sweetened drink mix is prepared by dry blending the above ingredients together and packaging in a container. In preparation for drinking, 7 g of powder can be added to from 4 to 8 oz of water or juice, followed by stirring.

Example 25

A calcium fortified shelf stable soybean milk can be prepared that has a 200 mg of calcium per liter of soy milk can be prepared as follows.

Soybean milk

| Weight % | Ingredients |
|---|---|
| 86% | filtered water |
| 9% | whole soy flour |
| 4% | fructose |
| 0.25% | sodium citrate |
| 0.20% | xanthan gum |
| 0.01% | Vitamins A & D |
| 0.70 | dicalciumhydroxy malate prepared in Example 23 |

A calcium fortified soybean milk can be prepared by heating the filtered water in a processing tank at about 85° C. After heating, soy flour is added under vigorous agitation, holding the temperature and mix until it is smooth and substantially lump free. Keeping the mixture under agitation, the vitamins, stabilizers, and dicalciumhydroxy malate prepared in accordance with Example 2 are then added. The composition is then pasteurized at 145° C. for 2 to 3 seconds, and homogenized at from 7000 to 8000 psi. The product can then be cooled to 0° C. and aseptically packaged into an appropriate container. Flavoring agents such as vanilla flavoring or chocolate cocoa powder can be added to enhance the taste characteristics, if desired.

While the invention has been described with reference to certain preferred embodiments and examples, those skilled in the art will appreciate that various modifications, changes, omissions, and substitutions can be made without departing from the spirit of the invention. It is therefore intended that the invention be limited only by the scope of the appended claims.

What is claimed is:

1. A mineral fortified food matrix, comprising:
a dimetalhydroxy malate composition; and
a food matrix fortified with the dimetalhydroxy malate composition.

2. A mineral fortified food matrix as in claim 1, wherein the dimetalhydroxy malate composition is a dicalciumhydroxy malate having the structure:

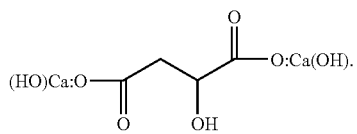

3. A mineral fortified food matrix as in claim 2, wherein the food matrix is further fortified by a second nutritionally relevant metal source.

4. A mineral fortified food matrix as in claim 3, wherein the second nutritionally relevant metal source is an iron source.

5. A mineral fortified food matrix as in claim 4, wherein the iron source is an iron amino acid chelate.

6. A mineral fortified food matrix as in claim 1, wherein the food matrix is a natural cereal grain.

7. A mineral fortified food matrix as in claim 1, wherein the food matrix is a processed cereal grain.

8. A mineral fortified food matrix as in claim 1, wherein the food matrix is a beverage.

9. A mineral fortified food matrix as in claim 1, wherein the food matrix is a dry beverage mix.

10. A mineral fortified food matrix as in claim 1, wherein the food matrix is an oleaginous or dairy product.

11. A mineral fortified food matrix as in claim 1, wherein each metal of the dimetalhydroxy malate is independently a nutritionally relevant metal selected from the group consisting of copper, zinc, manganese, iron, magnesium, calcium, and combinations thereof.

12. A method of administering a mineral in a bioavailable form to a warm-blooded animal, comprising:
fortifying a food matrix with a dimetalhydroxy malate composition; and
orally administering the food matrix fortified with the dimetalhydroxy malate composition to a warm-blooded animal.

13. A method as in claim 12, wherein the dimetalhydroxy malate composition is a dicalciumhydroxy malate composition having the structure:

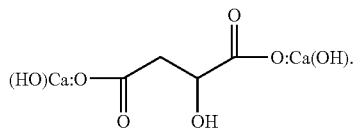

14. A method as in claim 12, further comprising the step of fortifying the food matrix with a second nutritionally relevant metal source prior to administering.

15. A method as in claim 14, wherein the second nutritionally relevant metal source is an iron source.

16. A method as in claim 15, wherein the iron source is an iron amino acid chelate.

17. A method as in claim 12, wherein the food matrix is selected from the group consisting of natural cereal grains, processed cereal grains, energy bars, beverages, dry beverage mixes, oleaginous foods, and dairy products.

18. A method as in claim 12, wherein each metal of the dimetalhydroxy malate is independently a nutritionally relevant metal selected from the group consisting of copper, zinc, manganese, iron, magnesium, calcium, and combinations thereof.

19. A calcium fortified food matrix, comprising:
a dicalciumhydroxy malate composition having the structure:

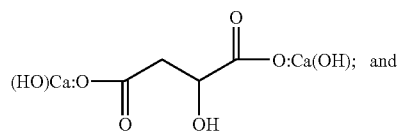

a food matrix fortified with the dicalciumhydroxy malate composition.

20. A calcium fortified food matrix as in claim 19, wherein the food matrix is further fortified with an iron amino acid chelate.

21. A method of administering calcium in a bioavailable form to a warm-blooded animal, comprising:
fortifying a food matrix with a dicalciumhydroxy malate composition having the structure:

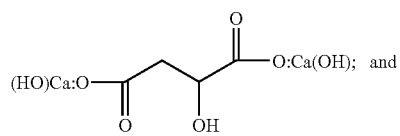

orally administering the food matrix fortified with the dicalciumhydroxy malate composition to a warm-blooded animal.

22. A method as in claim 21, further comprising the step of fortifying the food matrix with an iron amino acid chelate prior to administering.

* * * * *